(12) United States Patent
Kakuma

(10) Patent No.: US 10,433,730 B2
(45) Date of Patent: Oct. 8, 2019

(54) OPTICAL COHERENCE TOMOGRAPHIC IMAGE GENERATION APPARATUS

(71) Applicant: THE YOSHIDA DENTAL MFG. CO., LTD., Tokyo (JP)

(72) Inventor: Hideo Kakuma, Tokyo (JP)

(73) Assignee: The Yoshida Dental Manufacturing Company, Ltd., Tokyo (JP)

(*) Notice: Subject to any disclaimer, the term of this patent is extended or adjusted under 35 U.S.C. 154(b) by 0 days.

(21) Appl. No.: 15/767,579

(22) PCT Filed: Aug. 25, 2016

(86) PCT No.: PCT/JP2016/074749
§ 371 (c)(1),
(2) Date: Apr. 11, 2018

(87) PCT Pub. No.: WO2017/064928
PCT Pub. Date: Apr. 20, 2017

(65) Prior Publication Data
US 2018/0310825 A1    Nov. 1, 2018

(30) Foreign Application Priority Data
Oct. 13, 2015  (JP) ................................ 2015-202180

(51) Int. Cl.
*A61B 5/00*     (2006.01)
*A61B 1/00*     (2006.01)
(Continued)

(52) U.S. Cl.
CPC ........ *A61B 5/0066* (2013.01); *A61B 1/00006* (2013.01); *A61B 1/00009* (2013.01);
(Continued)

(58) Field of Classification Search
CPC ............................ A61B 5/0066; A61B 5/0088
See application file for complete search history.

(56) References Cited

U.S. PATENT DOCUMENTS

2008/0062429 A1* 3/2008 Liang ................. A61B 1/00039
356/497
2010/0165291 A1* 7/2010 Sugita .................... A61B 3/102
351/206
(Continued)

FOREIGN PATENT DOCUMENTS

JP    2012-024551    2/2012
JP    2012-211797    11/2012

OTHER PUBLICATIONS

International Search Report and Written Opinion received in connection with international application No. PCT/JP2016/074749; dated Nov. 22, 2016. (with English translation of the international search report).

*Primary Examiner* — Shawn Decenzo
(74) *Attorney, Agent, or Firm* — The Marbury Law Group, PLLC

(57) ABSTRACT

An optical coherence tomographic image generation apparatus includes: a probe including a two-dimensional scanning mechanism therein reflecting a beam incident from one of sides of the probe while a position of the beam is shifted by time-division drive; an optical unit that detects an optical coherent light created by interference between the reference beam and scattered light returned by reflection from the measuring object irradiated through the probe with the measurement beam to generate an optical coherent tomographic image from the detection signal of the coherent light acquired in a time base in one of first or second operation modes. In the first operation mode, scanning is performed parallel on an optical irradiation plane at the measuring object in a first direction. In the second operation mode, scanning is performed parallel on the optical irradiation plane at the measuring object in a second direction orthogonal with the first direction.

8 Claims, 7 Drawing Sheets"

(51) Int. Cl.
*A61B 1/045* (2006.01)
*A61B 1/247* (2006.01)

(52) U.S. Cl.
CPC .......... *A61B 1/00172* (2013.01); *A61B 1/045* (2013.01); *A61B 1/247* (2013.01); *A61B 5/0035* (2013.01); *A61B 5/0088* (2013.01)

(56) References Cited

U.S. PATENT DOCUMENTS

| | | | |
|---|---|---|---|
| 2012/0121158 A1* | 5/2012 | Sekine | G01N 21/4795 382/131 |
| 2013/0002711 A1* | 1/2013 | Sakagawa | A61B 3/0025 345/619 |
| 2013/0130191 A1* | 5/2013 | Iio | A61B 1/24 433/29 |
| 2013/0330686 A1* | 12/2013 | Kaji | A61B 5/0088 433/30 |
| 2014/0192323 A1* | 7/2014 | Kakuma | A61B 3/102 351/206 |

* cited by examiner

Front tooth, mouth

Front tooth, mouth

OPTICAL COHERENCE TOMOGRAPHIC IMAGE GENERATION APPARATUS

RELATED APPLICATIONS

This application is a U.S. national phase entry of international application no. PCT/JP2016/074749, filed on Aug. 25, 2016, which claims priority to Japanese Application No. 2015-202180, filed Oct. 13, 2015, the entire disclosures of which are incorporated herein by reference in their entireties.

TECHNICAL FIELD

The present invention relates to an optical coherence tomographic image generation apparatus, and particularly to an optical coherence tomographic image generation apparatus for measuring internal information in a measuring object while a user directs a tip of a nozzle of a probe griped by the user to a measuring object to measure internal information of the measuring object.

BACKGROUND ART

Conventionally, an optical coherence tomographic image generation apparatus for measuring internal information in a measuring object while a user grips a probe and directs a tip of a nozzle of a prove griped by the user to a measuring object to measure internal information of the measuring object, is known (see Patent Document 1). In this optical coherence tomographic image generation apparatus, when the user moves the tip of the nozzle of the griped probe to a measuring object, an optical coherence tomographic image or a three-D image is displayed as a real-time moving image following the motion in a pre-view mode for displaying the optical coherence tomographic image at a low resolution. Further, in a measuring mode for displaying an optical coherence tomographic image at a high resolution, the user brings the tip of the nozzle of the griped probe into contact with the measuring object to prevent by movement blur by the hand, etc.

Patent Document 1 disclosed a process of generating a tomographic image by the optical coherence tomographic image generation apparatus and a process of acquiring three-dimension information regarding internal information of the measuring object. Further, a monitor screen image is disclosed for displaying a tomographic image on a predetermined tomographic plane and a tomographic image on a tomographic plane orthogonal with the original tomographic plane. According to the process, when a lot of tomographic images are acquired, the tomographic images having tomographic planes such that the measuring object is sliced in a lateral direction when facing in a depth direction, three-dimensional information regarding the internal information of the measuring object can be obtained by overlaying the laterally sliced tomographic images in the in the longitudinal direction. Further, when the acquired three-dimensional information is sliced in a longitudinal direction when facing in the depth direction of the three-dimensional information, this provides a tomographic image on a tomographic plane orthogonal with the original tomographic plane.

PRIOR ART

Patent Document

Patent Document 1: JP 2012-211797

SUMMARY OF INVENTION

Problem to be Solved by Invention

However, there is a room for improving the hand movement compensation of an image in the conventional optical coherence tomographic image generation apparatus.

An aspect of the present invention provides an optical coherence tomographic image generation apparatus capable of reducing image disturbance due to the hand movement blur.

Means for Solving Problem

To solve the problem, the inventor studies the problem in various manners in the optical coherence tomographic image generation apparatus for measuring internal information of the measuring object to point the tip of the nozzle of the probe griped by the user. As a result, the inventor found that there is a close relation between disturbance of image due to hand movement blur and a method of acquiring three-dimensional information about the internal information of the measuring object. For example, when a lot of tomographic images are obtained on tomographic planes for slicing in the lateral direction when facing in a depth direction, time necessary for generating tomographic images on the tomographic plane orthogonal with the original tomographic plane is longer than time necessary for generating the tomographic image on the original tomographic plane, so that influence of the hand movement blur becomes larger.

An aspect of the present invention provides an optical coherence tomographic image generation apparatus comprising:

a probe including a grip part, a nozzle, and a two-dimensional scanning mechanism therein reflecting a light beam incident from one of sides of the grip part and the nozzle toward another side of the grip part and the nozzle while a position of the light beam is shifted by time-division drive;

an optical unit that divides a light beam emitted from a light source into a measurement light beam and a reference light beam and detects an optical coherent light created by making interference between the reference light beam and scattered light returned by reflection from the measuring object which is irradiated through the probe with the measurement light beam, the optical coherence tomographic image generation apparatus generating an optical coherent tomographic image from the detection signal of the coherent light acquired in a time base; and control means for switching between a first operation mode in which scanning is performed in parallel in a first direction on an optical irradiation plane at the measuring object and a second operation mode in which scanning is performed in parallel in a second direction on the optical irradiation plane at the measuring object, the second direction being orthogonal with the first direction.

According to the above-described configuration, tomographic images on tomographic planes orthogonal with each other by switching two operation modes of which scanning directions on the irradiation plane are orthogonal with each other to acquire the tomographic images on the two tomographic planes. In the first operation mode, a time period necessary for generating the tomographic image on such a tomographic plane that a measuring object is sliced in the second direction is longer than time period necessary for generating the tomographic image on such a tomographic plane that a measuring object is sliced in the first direction. On the other hand, a time period necessary for generating the tomographic image on such a tomographic plane that a measuring object is sliced in the second direction in the second operation mode is the same as the time period necessary for generating the tomographic image on such a tomographic plane that the measuring object is sliced in the first direction in the first operation mode. Accordingly, when the tomographic image on the tomographic plane that the measuring object is sliced in the second direction is displayed, a blur on the image due to hand movements can be reduced by selecting the second operation mode. Further, when a tomographic image on such a tomographic plane that the measuring object is sliced in the first direction is displayed, the blur on the image due to the hand movement can be reduced by selecting the first operation mode.

Further, in the optical coherence tomographic image generation apparatus according to the present invention, it is preferable that the two-dimensional scanning mechanism is configured with two galvanometer mirrors respectively having rotational axes which are orthogonal with each other.

According to the configuration, in the optical coherence tomographic image generation apparatus, a slight rotation operation and a stopping operation of the two galvanometer mirrors are made at a high speed in synchronous with the scanning speed of the light source, so that the blur on the tomographic image due to the hand movement can be reduced.

Further, it is preferable that a supporting member including a diagonal mirror for changing an optical axis is provided at a tip portion of the nozzle.

According to the configuration, it is possible to irradiate the molar with the light beam from the light source of the optical coherence tomographic image generation apparatus from an upper surface in a depth direction by inserting the supporting member to be attached to a tip portion of the nozzle of the probe griped by the user into the oral cavity of the patient and bringing the diagonal mirror into contact with the molar. This can acquire the tomographic image in which the blur in the image due to the movement of the hand is reduced, as a tomographic image on the tomographic plane in a depth direction of the molar.

Advantageous Effect of Invention

An aspect of the present invention can provide suppression of disturbance of the image due to the hand movements.

BRIEF DESCRIPTION OF DRAWINGS

FIG. 2A is a side view of a main part of the probe, FIG. 2B is an enlarged perspective view of a supporter at a tip of the probe, and FIG. 2C is an enlarged central cross section view of the supporter.

FIGS. 7A and 7B show drawings illustrating the two dimensional scanning, wherein FIG. 7A shows a relation between a teeth to be measured and a scanning direction in a first operation mode, and FIG. 7B shows a relation between a molar and a scanning direction.

FIGS. 8A to 8D show drawings illustrating the two-dimensional scanning, wherein FIG. 8A shows scanning on a reflection surface of the diagonal mirror in the first operation mode, FIG. 8B shows scanning on an upper plane of the molar in the first operation mode, FIG. 8C shows scanning on a reflection surface in the second operation mode, and FIG. 8D shows scanning on an upper surface of the molar in the second mode.

MODES FOR CARRYING OUT INVENTION

Referring to drawings, embodiments of an optical coherence tomographic image generation apparatus according to the present invention are described below.

Figure 1:
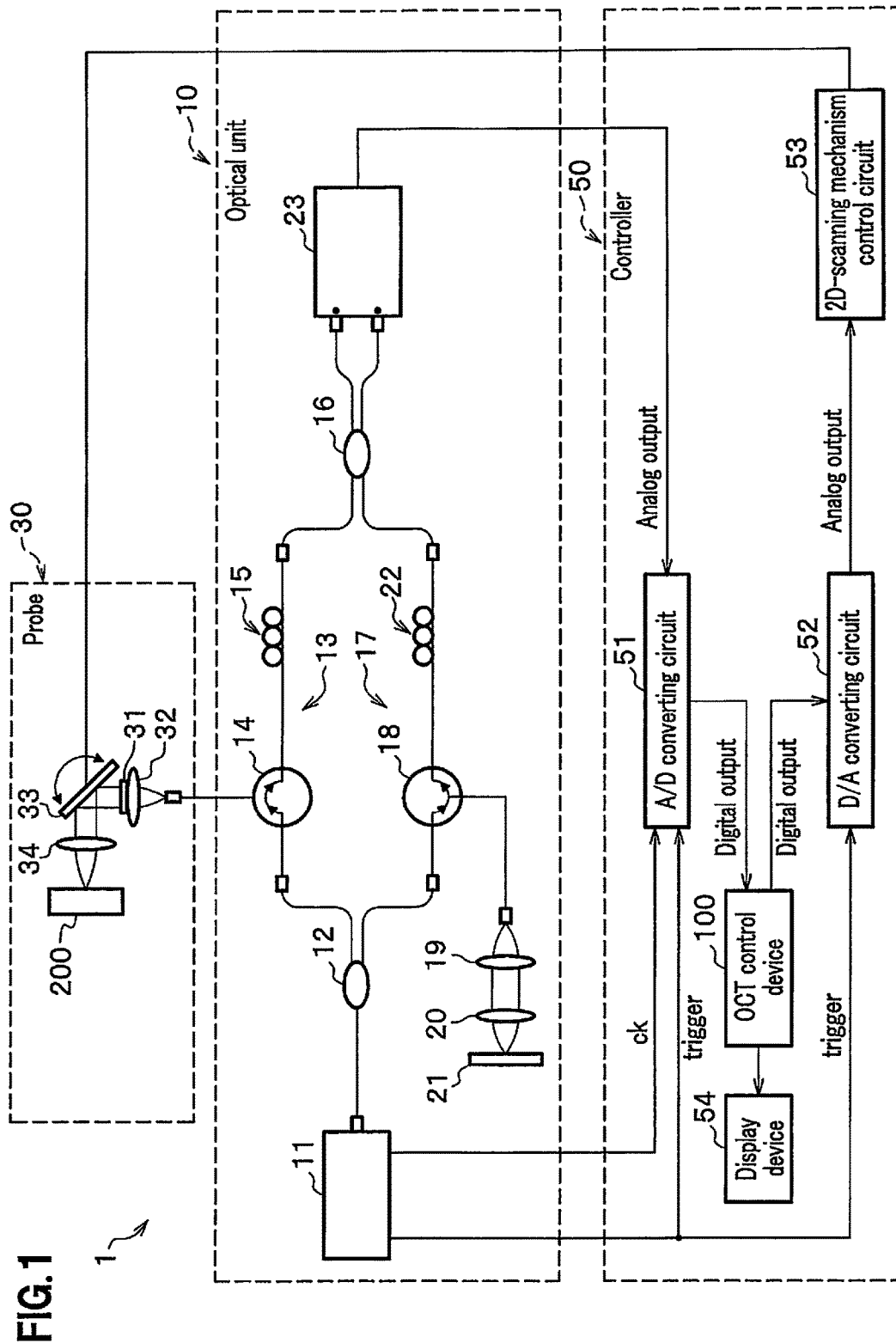
FIG. 1 is a block diagram schematically showing an optical coherence tomographic image generation apparatus according to an embodiment of the present invention.

As described in FIG. 1, an optical coherence tomographic image generation apparatus 1 mainly includes an optical unit 10, a probe 30, and a controller 50 to generate an optical coherence tomographic image from a detection signal of interference light beam detected in time base.

The optical unit 10 includes a light source, an optical system, and a detector applicable to a generally used optical coherence tomography of various methods. As shown in FIG. 1, the optical unit 10 includes a light source 11 for periodically irradiating a measuring object 200 with a laser light and a detector 23 for detecting internal information of the measuring object 200. The optical unit 10 includes optical fibers and various optical components, etc. between the light source 11 and the detector 23. As the light source 11, for example, a laser light emitting device of SS-OCT (Swept Source Optical Coherence Tomography) method. The measuring object (subject) 200 is, for example, a tooth.

Outline of the optical unit 10 is described below.

Light beam emitted by the light source 11 is divided into a measuring light beam and a reference light beam by a coupler 12 as a light dividing means. The measuring light beam is inputted into the probe 30 by a circulator 14. When a shutter 31 of the probe 30 is in an open state, the measuring light beam is converged on the measuring object 200 by a condenser lens 34. The light beam is scattered and reflected on the converged point and then scattered light and reflected light enters the condenser lens 34 again and returns to a circulator 14 via a two-dimensional scanning mechanism 33 and a collimator lens 32. The returned measuring light beam is inputted into the detector 23 via a coupler 16.

On the other hand, the reference light beam divided by the coupler 12 is converged by a condenser lens 20 on a reference mirror 21 via a circulator 18 and a collimator lens 19 in a reference arm 17 and reflected at the converged point. The reflected light beam returns to the circulator 18 transmitting through the condenser lens 20 and the collimator lens 19 again. The returned reference light beam is inputted into the detector 23 via the coupler 16. More specifically, the coupler 16 combines the measuring light scattered and reflected at the measuring object 200 with the reference light beam reflected by the reference mirror 21. The interference light beam (interference light) is detected by the detector 23 as internal information. Further, a polarization controller 15 in a sampling arm 13 and a polarization controller 22 in the reference arm 17 are installed to return a polarized state of light generated in the optical coherence tomographic image generation apparatus 1 including the probe 30 to a less polarized state.

The probe 30 includes the two-dimensional scanning mechanism 33 for two-dimensional scanning with a laser beam to introduce the laser beam from the optical unit 10 into the measuring object 200 and the light reflected by the measuring object 200 into the optical unit 10. The probe 30 is connected to the optical unit 10 with an optical fiber for transmitting a light signal and connected to the controller 50 through an electric signal wiring. When photographing, the user grips the probe 30 and brings the probe 30 into contact with the patient to avoid hand movement blur or the like.

Figure 2A:
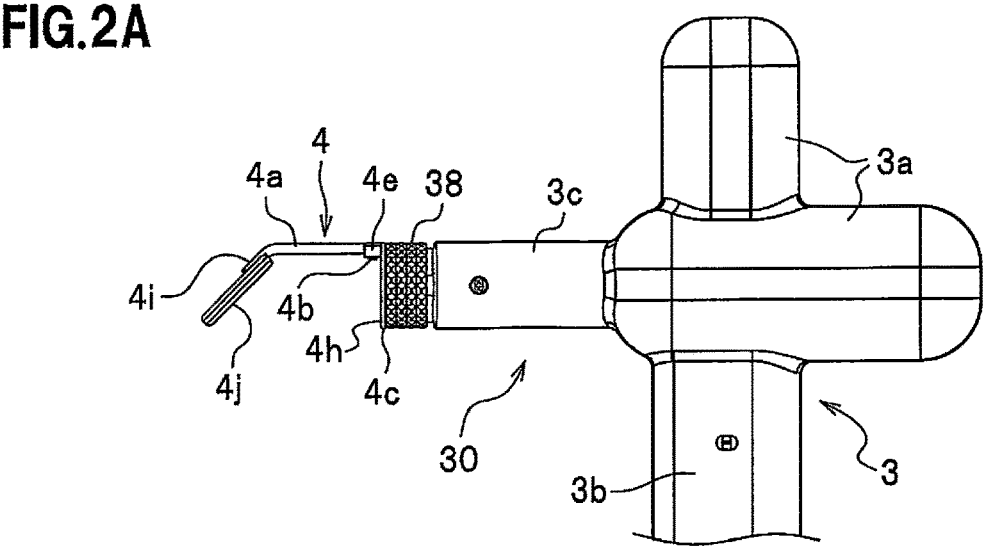
FIGS. 2A to 2C are drawings showing a probe, where

Components of the probe 30, the optical filers, and electric signal wiring are installed in a housing 3 as shown in FIG. 2(a), for example. The housing 3 houses, for example, a scanning mechanism housing part 3a, a grip part 3b, and a nozzle 3c.

The scanning mechanism housing parts 3a are parts for housing the two-dimensional scanning mechanism 33 (see FIG. 1).

The grip part 3b is a part that the user grips with the hand in which the collimator lens 32 (see FIG. 3) etc. are disposed in the grip part 3b. At predetermined positions of the grip part 3b, a plurality of operation buttons are disposed (omitted in the drawings). The plurality of the buttons include, for example, a button for making the shutter 31 of the probe 30 in an open state, a button for starting the open state of the shutter 31, and a button for starting the measurement (photographing).

A supporting body 4 is attached to the tip of the nozzle 3c through a tip member 38 detachably (replaceable) and rotatably. Further, the nozzle 3c houses the condenser lens 34 (see FIG. 3) for collecting the scanning light beam scanned by the two-dimensional scanning mechanism 33, etc. thereinside.

Figure 2B:
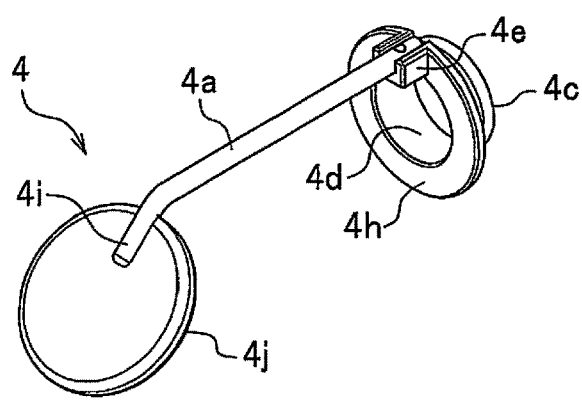
Figure 2C:
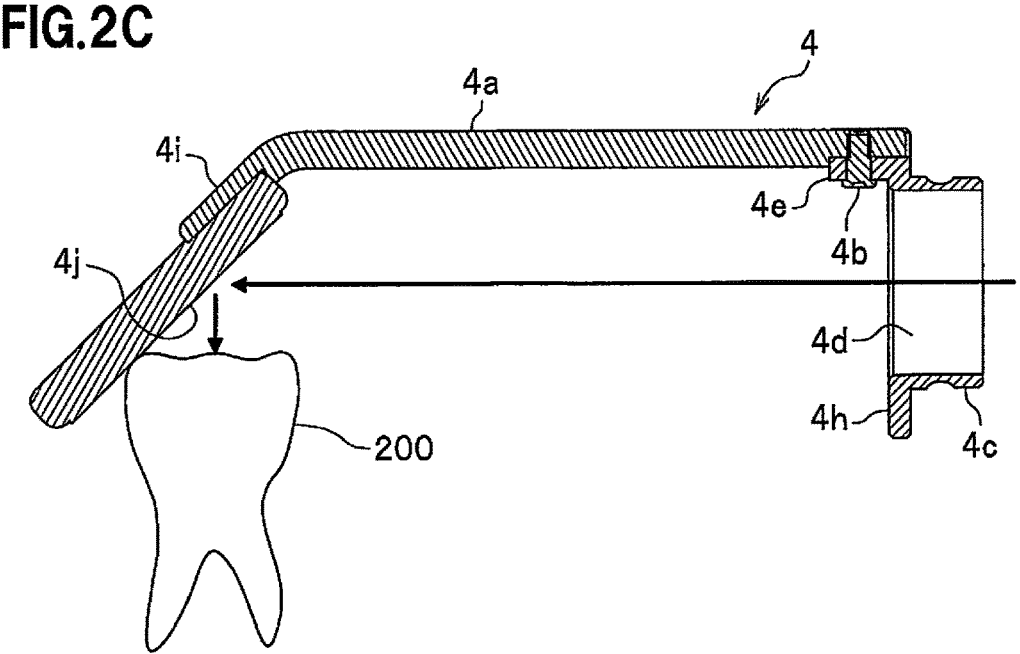

In the embodiment, as shown in FIGS. 2A, 2B, and 2C, the supporting body 4 mainly includes a coupling tubular member 4c inserted into the housing 3 detachably, a rod part 4a, a connecting part 4b for connecting the rod part 4a to the coupling tubular member 4c, and a diagonal mirror 4j. The supporting body 4 is made of a stainless steel or the like.

The coupling tubular member 4c is disposed in front of the condenser lens 34 and has an opening 4d for projecting the measuring light beam to the measuring object 200 and collects the scattered light. In the coupling tubular member 4c, a base part of the rod part 4a is coupled to a connecting part 4e on an upper front side of a flange part 4h. The rod part 4a is fixed to the coupling tubular member 4c by the connecting part 4b detachably. The rod part 4a includes a bending part 4i including a tip part which is bent downward by about 45 degrees. The diagonal mirror 4j is connected to the bending part 4i. The diagonal mirror 4j is a reflection mirror for changing an optical axis of the condenser lens 34 to a direction perpendicular to the original optical axis by 90 degrees.

When photographing is made with the probe 30, the probe 30 can be supported in a stable state by bringing the supporting body 4 connected to the tip part of the housing 3 in contact to the measuring object 200 as shown in FIG. 2 (c). The supporting body 4 is suitable for taking a tomographic image of, for example, a tissue in an oral cavity, a masticating surface, a surface on the tongue, or a surface on the side of the cheek of the molars, and a tomographic image of a surface on the side of the tongue of a front tooth.

Further, the supporting body 4 can be kept always clean by replacement with another supporting body 4 which is new or cleaned.

Figure 3:
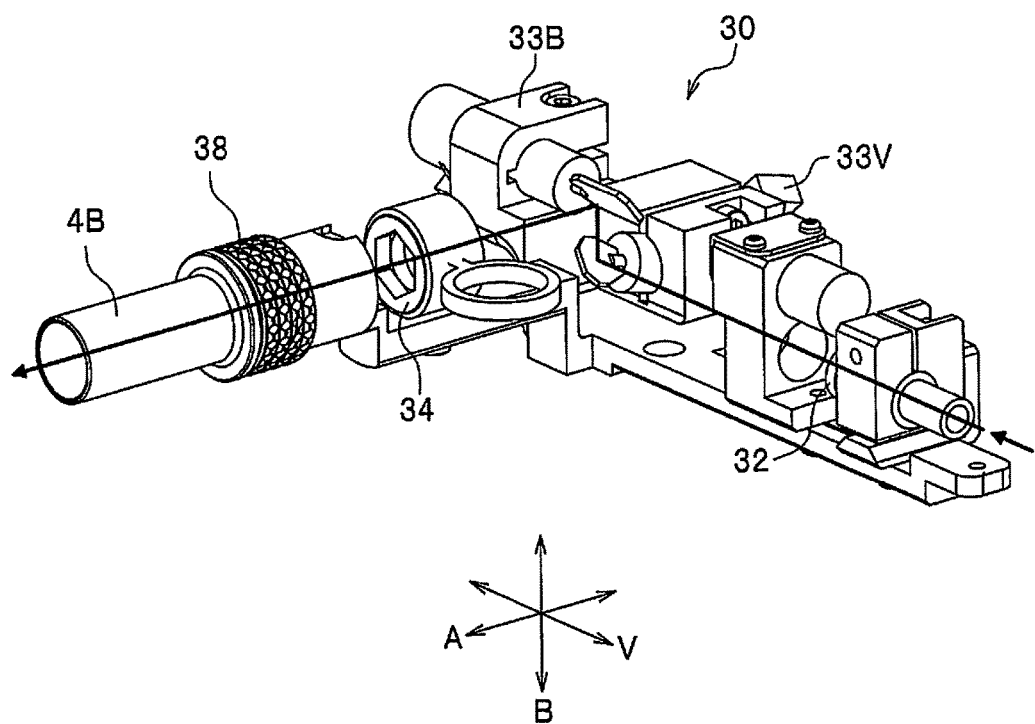
FIG. 3 is an outline view of light paths of laser beam inside the probe.

In the probe 30, the supporting body 4 is replaced with, for example, a supporting body 4B having tubular cylinder type shown in FIG. 3 in accordance with the use of photographing. Further, another type of the supporting body which is made by removing the bending part 4i and the diagonal mirror 4j from the supporting body 4 is prepared, and photographing can be performed by bringing the tip part of the rod part 4a having a straight shape in contact with the front tooth.

The two-dimensional scanning mechanism 33 is a part reflecting a light beam incident from either side of the grip part 3b or the nozzle 3c with successive positional shifts by time-division driving to another side. In the embodiment, the two-dimensional scanning mechanism 33 includes, as shown in FIG. 3, a galvanometer mirror 33V and a galvanometer mirror 33B of which axes are orthogonal with each other as shown in FIG. 3. Accordingly, in the embodiment, the two scanning mechanism housing parts 3a are disposed in the housing 3. Further, the A-axis, the B-axis, and the V-axis shown in FIG. 3 are orthogonal with each other.

The galvanometer mirror 33B rotates the mirror surface by a predetermined angle about the axis along the V-axis in FIG. 3 by motor driving. For example, the light beam incident from a side of the collimator lens 32 to the galvanometer mirror 33B receives a parallel shift of the projection position along the B-axis in FIG. 3 by rotation of the mirror surface of the galvanometer mirror 33B and is emitted through the condenser lens 34. A direction along the B-axis corresponds to a left and right direction at the measuring object (see FIG. 4).

The galvanometer mirror 33V rotates a mirror surface of the galvanometer mirror 33V about an axis along the A-axis in FIG. 3 by motor drive. For example, the light incident from a side of the collimator lens 32 receives a parallel shift of the projection position along the V-axis in FIG. 3 by rotation of the mirror surface of the galvanometer mirror 33V and is emitted through the condenser lens 34. A direction along the B-axis corresponds to a left and right direction at the measuring object 200 (see FIG. 4). The direction along the V-axis corresponds to the vertical direction in FIG. 4 at the measuring object 200 (see FIG. 4).

As shown in FIG. 1, the controller 50 includes an A/D converting circuit 51, a D/A converting circuit 52, a two-dimensional scanning mechanism control circuit 53, a display device 54, and an OCT (Optical Coherence Tomography) control device 100.

The A/D converting circuit 51 is a circuit for converting an analog output signal of the detector 23 into a digital signal. In the embodiment, the A/D converting circuit 51 starts acquiring a signal synchronously with a trigger (trigger) outputted by the laser emitting device as the light source 11, acquires the analog output signal of the detector 23 in response to timing of a clock signal ck similarly outputted by the laser emitting device, and converts the analog output signal into a digital signal. The digital signal is inputted into the OCT control device 100.

The D/A converting circuit 52 is a circuit for converting the digital output signal of the OCT control device 100 into an analog signal. In the embodiment, the D/A converting circuit 52 converts the digital signal of the OCT control device 100 into the analog signal synchronously with the trigger (trigger) outputted by the light source 11. The analog signal is inputted into the two-dimensional scanning mechanism control circuit 53.

The two-dimensional scanning mechanism control circuit 53 is a driver for controlling the two-dimensional scanning mechanism 33 in the probe 30. The two-dimensional scanning mechanism control circuit 53 outputs a motor drive signal for controlling between driving and stopping the motors of the galvanometer mirror 33B or the galvanometer mirror 33V synchronously with an output cycle of the laser beam emitted by the light source 11 on the basis of the analog output signal of the OCT control device 100.

The two-dimensional scanning mechanism control circuit 53 performs a process of changing the angle of the mirror surface by rotating a rotation shaft of the galvanometer mirror 33B and a process of changing the angle of the mirror surface by rotating the rotation shaft of the galvanometer mirror 33V at different timings.

The display device 54 is a device for displaying an optical coherent tomographic image (hereinafter may be simple referred to as topographical image) generated by the OCT control device 100. The display device 54 comprises, for example, a liquid crystal display (LCD: Liquid Crystal Display), etc.

The OCT control device 100 performs measurement by controlling the two-dimensional scanning mechanism 33 synchronously with the light beam emitted by the light source 11 as well as performs control for generating the tomographic image, etc of the measuring object 200 from data obtained by converting the detection signal of the detector 23. The topographical image, etc. can be generated by a known method of generating optical coherence tomographic image, etc. In addition, the tomographic image, etc. may be generated by the method disclosed in JP2012-211797 A.

The OCT control device 100 comprises a computer including, for example, a CPU (Central Processing Unit) or GPU (Graphics Processing Unit), a RAM (Random Access Memory), a ROM (Read Only Memory), a hard disk drive, and an input/output interface.

The OCT control device 100 has a first operation mode for scanning in a lateral direction (first direction) in parallel on an irradiated plane on the measuring object 200 and a second operation mode for scanning in parallel in the longitudinal direction (second direction) orthogonal with the lateral direction (the first direction) in which the first operation mode and the second operation mode can be switched therebetween. For example, the user can manually switch the operation mode of the two-dimensional scanning mechanism 33 with, for example, a user interface such as a mouse, etc connected to the OCT control device 100. Further, a button switch for the switching may be installed at a predetermined position of the grip part 3b of the probe 30.

When the OCT control device 100 sends a control signal of the first operation mode to the two-dimensional scanning mechanism control circuit 53, the two-dimensional scanning mechanism control circuit 53 performs a control repeating a one-dimensional scanning in a left-right direction (the lateral direction) on the irradiated plane generated by rotation of the galvanometer mirror 33B and a small positional shift on the irradiated plane 9 made by a small rotation of the galvanometer mirror 33V in the up-down direction (the vertical direction).

When the OCT control device 100 sends a control signal of the second operation mode to the two-dimensional scanning mechanism control circuit 53, the two-dimensional scanning mechanism control circuit 53 performs a control repeating: a one-dimensional scanning in an up-down direction (the vertical direction) on the illuminated plane generated by rotation of the galvanometer mirror 33V; and a small positional shift on the irradiated plane 9 made by a small rotation of the galvanometer mirror 33B in the left-right direction (the lateral direction).

Next, with reference to FIGS. 4, 5, and 6 (occasionally, FIGS. 1, 2A, 2B, and 2C a process of acquiring three-dimensional information of the internal information of the measuring object by the OCT control device 100 (hereinafter referred to as three-dimensional scanning) is described below.

Figure 4:
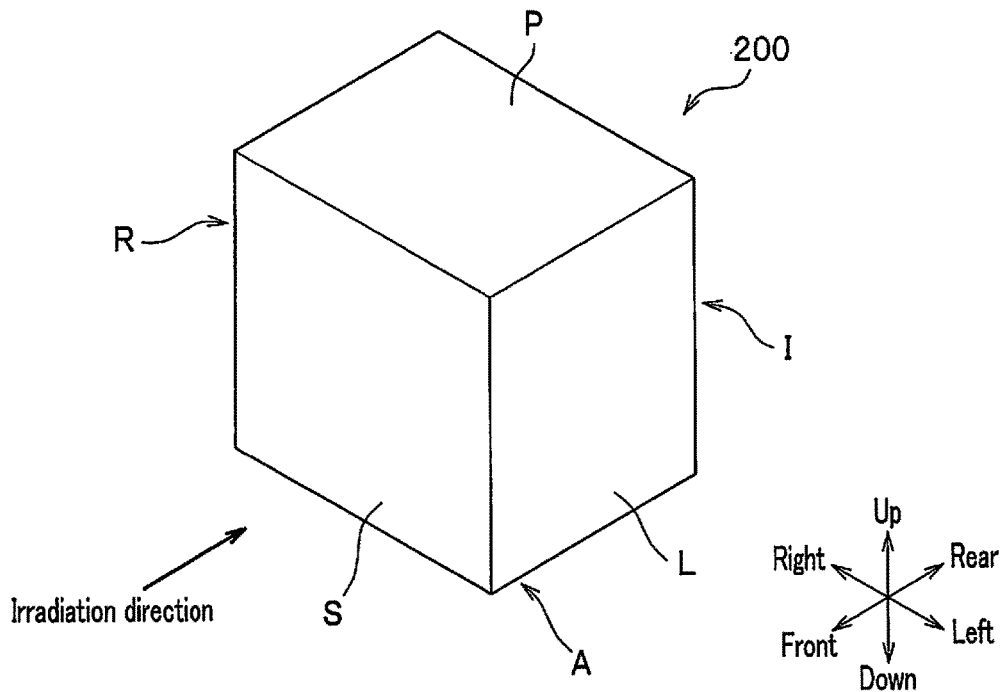
FIG. 4 is an explanatory drawing of a two-dimensional scanning and shows a relation between a light emitting direction and a direction of the measuring object.

The description is made with assumption that a shape of the measuring object 200 is a rectangular parallelepiped as shown in FIG. 4. Size of the rectangular parallelepiped are, for example, 10 mm in lateral size (width)×10 mm in vertical size (height)×8 mm in depth size.

Here, it is assumed that a front surface, a rear surface, a left side surface, a right side surface, a bottom surface, and an upper surface are referred to as an S surface, an I surface, an L surface, an R surface, an A surface, and a P surface, respectively. In a case where a measuring object 200 is a front tooth of the patient, it is preferable that a surface outside the front tooth (S surface) is irradiated with the measurement light beam (laser beam) in an irradiation direction as shown in FIG. 4.

On the other hand, when the measuring object 200 is a molar, it is preferable that the masticating surface (P surface) of the molar is irradiated after changing the irradiation direction of the measurement light beam to a downward direction. The irradiation direction of the measurement light beam can be changed by replacing the supporting body 4 at the tip of the nozzle 3c of the probe 30. Here, as an example, description is made below with assumption that the measuring object 200 is irradiated in the irradiation direction shown in FIG. 4.

Figure 5:
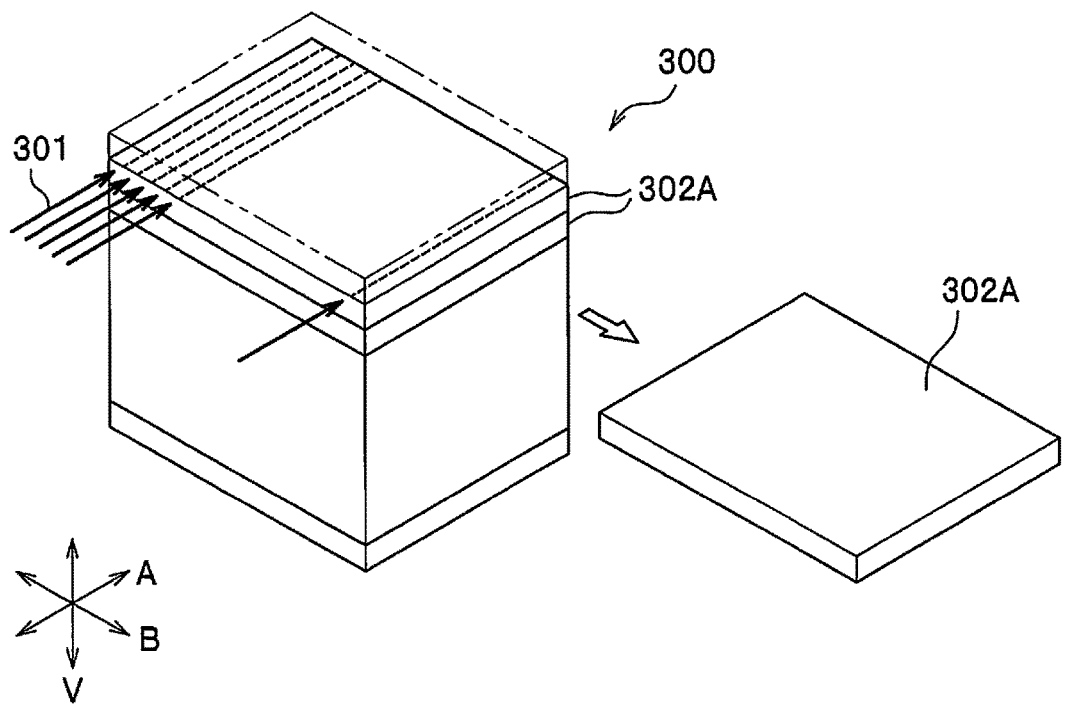
FIG. 5 is a drawing showing a relation between a first operation mode and optical coherence tomographic image.
Figure 6:
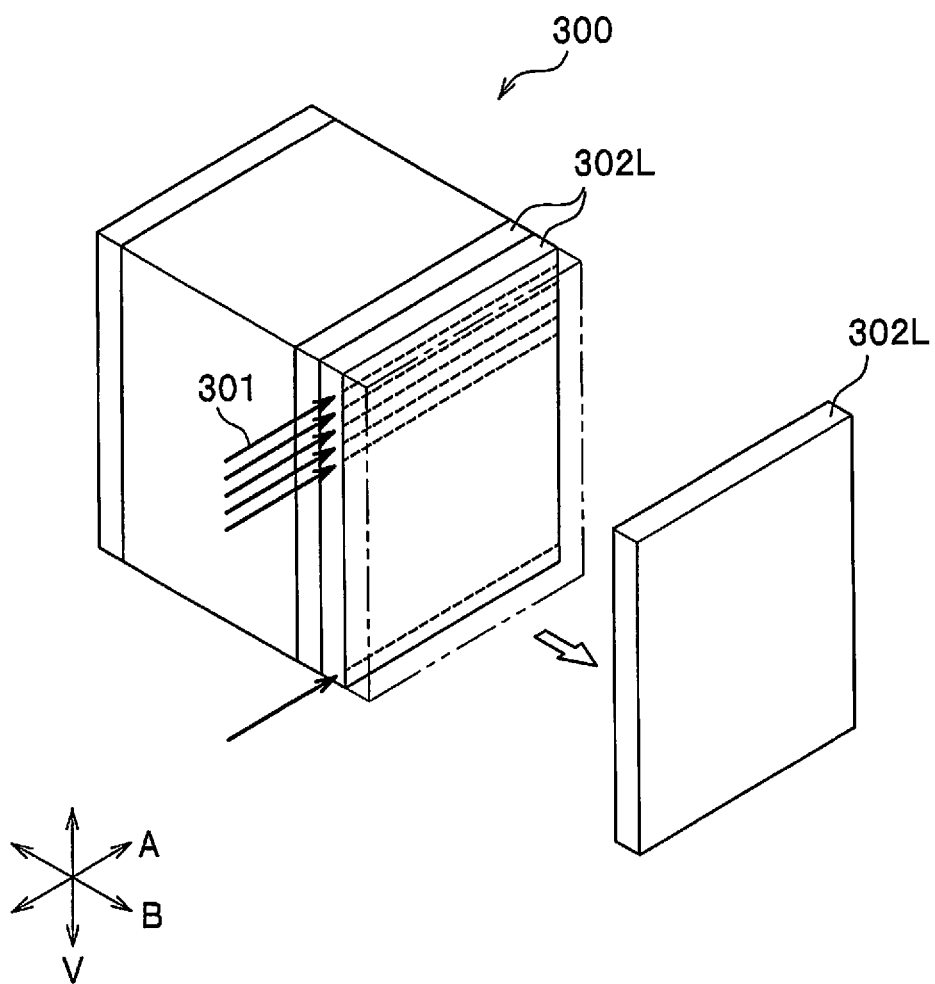
FIG. 6 is a drawing illustrating two-dimensional scanning to show a relation between a second operation mode for making scanning in parallel in the longitudinal direction and an optical coherence tomographic image.

An A axis, a B axis, and a V axis shown in FIG. 5 indicate directions along the A axis, the B axis, and the V axis in the probe 30 shown in FIG. 3. Here, it is assumed that the A-axis direction is an irradiation direction of the laser beam to the S-surface of the measuring object 200 shown in FIG. 4. It is assumed that the B-axis direction corresponds to the left-right direction of the measuring object 200 shown in FIG. 4. Further, it is assumed that the V-axis corresponds to the up-down direction of the measuring object 200 shown in FIG. 4.

An A-scan line 301 schematically shows tomographic information (internal information) along a depth direction from the light beam irradiated plane (S surface) which is acquired by the OCT control device 100 while the measuring object 200 is irradiated with the light beam (measurement light beam) from the light source 11.

During the measurement, the measuring object 200 is irradiated with a light beam reflected by mirror surfaces of the galvanometer mirror 33V and the galvanometer mirror 33B. The reflected and scattered light returns on the same route as an optical signal which is detected as an electric signal which is used to create an image in which data of the A-scan line 301 is acquired.

The A-scan lines 301 indicate tomographic information (internal information) at a predetermined number of points along the A-axis shown in FIG. 5. For example, if it is assumed that a length in the depth direction at a region in which the internal information is undergone imaging in the measuring object 200 is 8 mm, it is preferable that, for example 2048 points are set in the distance of 8 mm for diagnosis.

Further, in the three-dimensional scanning, a predetermined number of points are previously set along the B-axis for making the A-scan lines 301. The number of the points can be appropriately set in accordance with a desired condition such as a resolution of the image to be visualized and time necessary for generating the image. For diagnosis, for example, 100 to 400 points are set in a distance of 10 mm.

In the first operation mode, the two-dimensional scanning mechanism control circuit 53 slightly rotates the shaft of the galvanometer mirror 336 to shift the irradiation position of the laser beam along the B-axis when the galvanometer mirror 33V is at a predetermined rotation angle. According to this operation, the OCT control device 100 can acquire data of the A-scan lines 301 at a predetermined number of points, which is main scanning.

An image processing means of the OCT control device 100 can acquire a tomographic image 302A by combining the predetermined number of the points of the A-scan lines 301, the tomographic image 302A indicating the internal information when the measuring object 200 is sliced in the lateral direction (left-right direction) and the depth direction. The tomographic image 302A is a tomographic image of the measuring object 200 shown in FIG. 4 made by lateral slicing which is in parallel with the bottom surface (A surface) of the measuring object 200.

Further, in the three-dimensional scan, a predetermined number of points are set along the V-axis for the A-scan lines 301. The number of the points can be determined similarly to the number of the points set along the B-axis.

During measurement, in the first mode, the two-dimensional scanning mechanism control circuit 53 successively acquires data of the A-scan lines 301 while the irradiation point of the laser beam is shifted along the B-axis. The two-dimensional scanning mechanism control circuit 53 slightly rotates the shaft of the galvanometer mirror 33V when data of the A-scan lines 301 at the predetermined number of points has been acquired to shift the irradiation point of the laser beam in the vertical direction (up-down direction) along the V-axis, which is subscanning. The tomographic images of the lateral slicing (the tomographic images 302A) are piled in the vertical direction along the V-axis, so that three-dimensional information 300 including the internal information of the measuring object 200 can be acquired. Three-dimensional information 300 is data which is created by integrating the tomographic image information three-dimensionally scanning the internal of the measuring object 200. When the three-dimensional information 300 is sliced in the V-axis direction (vertical direction) toward the A-axis direction (depth direction), it is possible to generate a tomographic image 302L orthogonal with the original tomographic plane.

In the first mode, time necessary for generating the tomographic image 302A varies in accordance with the conditions of the number of the set points for two-dimensional scanning, a scanning speed, etc. of the light source 11.

As an example, time necessary for generating the tomographic image in the next condition 1 is estimated.
(Condition 1)

The condition 1 is that 2048 points are set in a distance of 8 mm along the A-axis, 400 points are set in a distance of 10 mm along the B-axis, and 400 points are set in a distance of 10 mm along the V-axis, and a light source having a center wavelength of 1310 nm, sweeping wavelength width of 140 nm, and the scanning speed of 50 kHz, is used.

In the condition 1, the time period necessary for acquiring the data of the A-scan line 301 is 20 μs and the time period necessary for generating the tomographic image 302A becomes 20 μs×400=8 ms. In the first operation mode, the time period necessary for generating the tomographic image 302A is relatively short, so that influence of hand movement is small. The tomographic image 302A displayed on the display device 54 does not include a blur due to hand movement, so that the image can be preferably used for diagnosis.

On the other hand, in the case where the tomographic image 302L (see FIG. 6) is generated on the basis of the tomographic image 302A in the first operation mode, the necessary time period is 8 ms×400=3.2 s.

The time period necessary for generating the tomographic image 302L is longer than the time period necessary for generating the tomographic image 302A, so that the influence of the hand movement blur becomes larger. When the tomographic image 302L is displayed on the display device 54, the hand movement blur become more distinguished than the case where the tomographic image 302A is displayed on the screen. Accordingly, in the first operation mode, it is allowed to generate the tomographic image 302L on the basis of the tomographic image 302A. However, it is preferable that the tomographic image 302L is not used for the image diagnosis. Instead, it is allowed that the tomographic image 302L generated in the second operation mode is used.

In the optical coherence tomographic image generation apparatus 1, the operation in the second operation mode is different from the operation in the first operation mode in that the operation order of the galvanometer mirror 33B and the galvanometer mirror 33V are exchanged. The A-scan lines 301 shown in FIG. 6 schematically show the tomographic information (internal information) at the predetermined number of points previously set along the depth direction from the light beam irradiation plane similarly to the A-scan lines 301 shown in FIG. 5.

In the second operation mode, the two-dimensional scanning mechanism control circuit 53 slightly rotates the galvanometer mirror 33V to shift the irradiation position of the laser beam when the galvanometer mirror 33B is at a predetermined rotation angle. According to this, the OCT control device 100 acquires the data of the predetermined number of the A-scan lines 301.

The image processing means of the OCT control device 100 can acquire a tomographic image 302L indicating the internal information when the measuring object 200 is sliced in the vertical direction (up-down direction) when facing in the depth direction by integrating the predetermined number of the points of the A-scan lines 301. The tomographic image 302L is a tomographic image made by longitudinally slicing on a tomographic plane which is in parallel with the left side surface (L surface) of the measuring object 200 shown in FIG. 4.

In the second operation mode, the two-dimensional scanning mechanism control circuit 53 successively acquires data of the A-scan lines 301 while shifting the irradiation position of the laser beam along the V axis. Whenever having acquired the data of the A-scan lines 301 of the predetermined number of points (for example, 400 points), the two-dimensional scanning mechanism control circuit 53 slightly rotates the shaft of the galvanometer mirror 33B to shift the irradiation point of the laser beam in the lateral direction (left-right direction) along the B axis. Then, the three-dimensional information 300 regarding the internal information of the measuring object 200 can be acquired similarly to the first operation mode by piling the longitudinally sliced tomographic image (the tomographic image 302L). In addition, it is possible to generate the tomographic image 302A (see FIG. 5) on the tomographic plane orthogonal with the original tomographic plane by slicing the three-dimensional information 300 in the B-axis direction (lateral direction) toward the A-axis direction (depth direction), In the second operation mode, a time period necessary for generating the tomographic image 302L in the second operation mode is estimated in the condition 1 described earlier.

In the condition 1, the time period necessary for acquiring the data of the A-scan lines 301 is 20 μs, and the time period necessary for generating the tomographic image 302L is 20 μs×400=8 ms. In this second operation mode, influence of the hand movement is a small degree because the time period for generating the tomographic image 302L is the same as that of the tomographic image 302A in the first operation mode, which is a short period. Accordingly, the tomographic image 302L displayed on the display device 54 in the second operation mode is free from blur on the image due to the hand movement and can be preferably used for the image diagnosis.

Next, a flow of measurement by the optical coherence tomographic image generation apparatus 1 is described below referring to FIGS. 7A and 7B and FIGS. 8A, 8B, 8C, and 8D (occasionally referring to other figures).

After turning on a power switch (not shown), the user sets the operation mode of the two-dimensional scanning mechanism 33 to, for example, the first operation mode using a user interface. Next, the user operates a button for bringing the shutter 31 shown in FIG. 1 in the open state, and then operates a button to start the measurement (photographing).

In the case where the measuring object 200 is a molar, after inserting the supporting body 4 connected to the tip part of the griped probe 30 into the oral cavity of the patient in front of the patient, the user brings the supporting body 4 in contact with the molar (measuring object 200) as shown in FIG. 2C to make positioning for the patient and then performs the measurement. Incidentally, FIGS. 7A and 7B schematically show upper and lower tooth rows, and it is impossible to insert the supporting body 4 connected to the tip part of the probe 30 from a side of the patient.

Figure 7A:
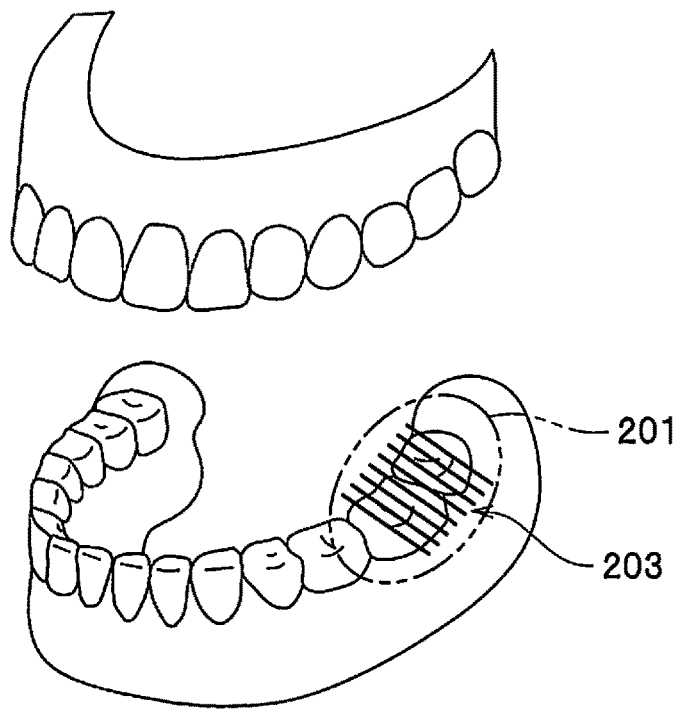
Figure 7B:
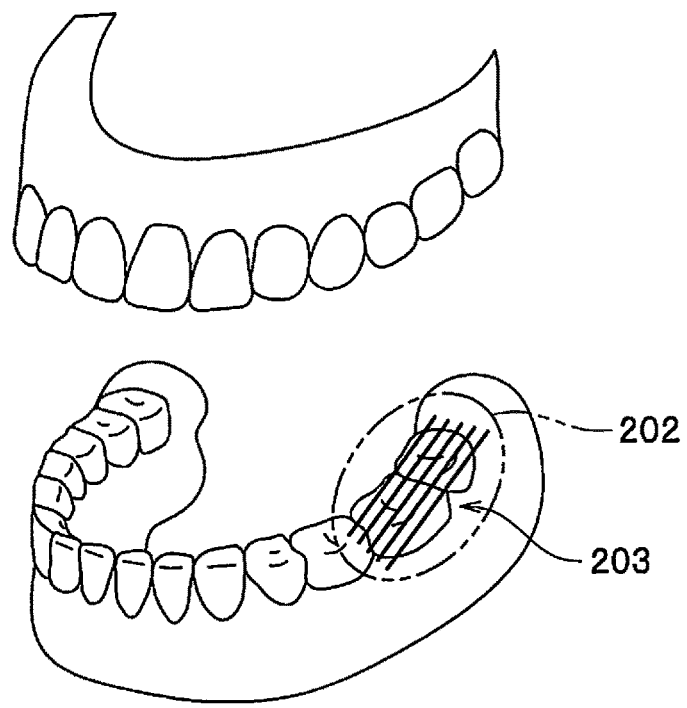

The optical coherence tomographic image generation apparatus 1 performs an operation in accordance with the setting and in the first operation mode scans the light beam irradiation plane at molars (masticating surface) in parallel in a lateral direction as shown in FIG. 7A. This can generate the tomographic image 302A. Incidentally, the masticating surface of the molars shown in FIGS. 7A and 7B corresponds to the P surface of the measuring object 200 when the irradiation direction of the measurement light beam shown in FIG. 4 is changed to the downward direction.

A specific example of the two-dimensional scanning in the first operation mode is described below referring to FIGS. 7A, 8A, and 8B (occasionally referring to other drawings).

Figure 8A:
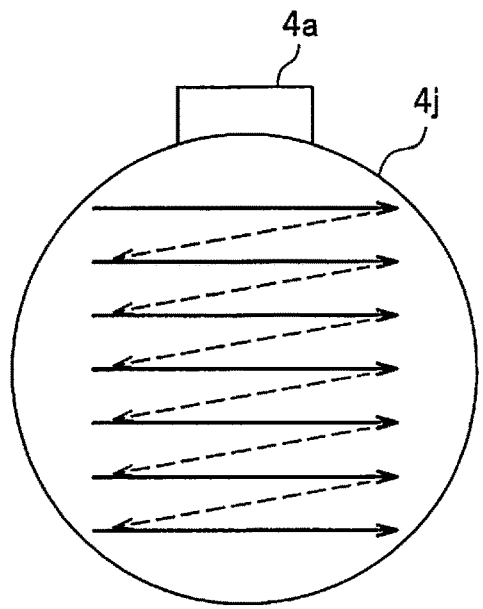

FIG. 8A shows a reflection surface of the diagonal mirror 4j of the supporting body 4 connected to the tip part of the probe 30. In FIG. 8A the rod part 4a of the supporting body 4 is disposed on the upper side, and the measuring object is disposed on the lower side. FIG. 8B shows a light beam irradiation plane 201 on the molars shown in FIG. 7A. In FIG. 8B, it is assumed that front teeth and a mouth of the patient are arranged on the lower side.

In the two-dimensional scanning mechanism 33, a mirror surface of the the galvanometer mirror 33B performs a reciprocating motion within a predetermined rotation angle range. This shifts the irradiation position of the light beam from the light source 11 along the B axis. As shown, the irradiation position of the light beam is shifted by outward scanning movement from the left side to the right side on the reflection surface of the diagonal mirror 4j and the light beam irradiation plane 201. Incidentally, the moving direction of the irradiation position of the light beam may be from the right side to the left side.

Further, in the two-dimensional scanning mechanism 33, the data acquired during returning movement within the predetermined rotation angle range of the mirror surface of the galvanometer mirror 33B is not used.

In the two-dimensional scanning mechanism 33, the mirror surface of the galvanometer mirror 33V performs reciprocating motion within a predetermined rotation angle range. This shifts the irradiation position of the light beam from the light source 11 along the V axis. Out of the movements, the movement during the outgoing pass shifts the irradiation position of the light beam, for example, from upside to the down side on the reflection surface of the diagonal mirror 4j, and on the light beam irradiation plane 201, shifts the irradiation position of the light beam, for example, from lower side (this side) to the upper side (back side). The shifting direction of the irradiation position of the light beam may be in an opposite direction.

Further in a case where the user sets the operation mode of the two-dimensional scanning mechanism 33 to, for example, the second operation mode using the user interface, the optical coherence tomographic image generation apparatus 1 operates as follows:

The optical coherence tomographic image generation apparatus 1 scans the measurement light beam in parallel in the vertical direction on the light beam irradiation plane (masticating surface) at the molars as shown in FIG. 7B. This can generate the tomographic image 302L.

A specific example of the two-dimensional scanning in the second mode is described below referring to FIG. 7B, FIGS. 8C and 8D (occasionally referring to other drawings).

Figure 8C:
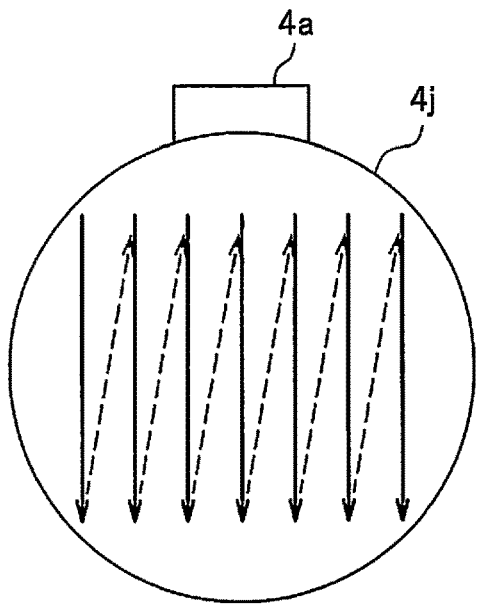
Figure 8B:
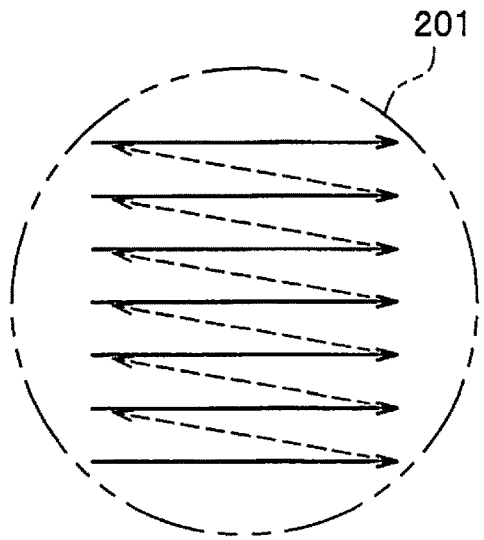
Figure 8D:
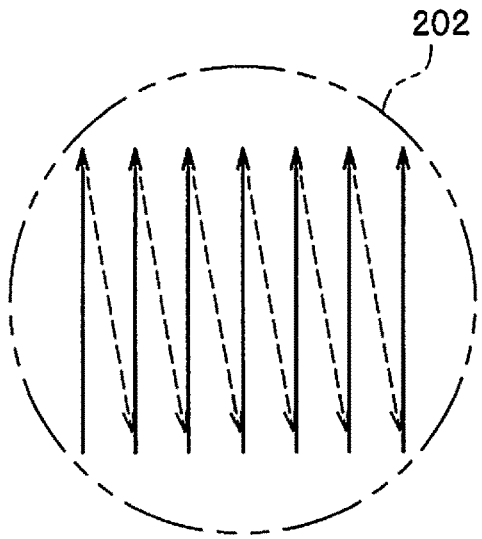

FIG. 8C shows the reflection surface of the diagonal mirror 4j of the supporting body 4 connected to the tip part of the probe 30. In FIG. 8C, the rod part 4a of the supporting body 4 is disposed on the upper side, and the measuring object is disposed on the lower side. FIG. 8D shows a light beam irradiation plane 202 at the molars shown in FIG. 7B. In FIG. 8D, it is assumed that the front teeth and the mouth are disposed on the lower side.

In the two-dimensional scanning mechanism 33, a mirror surface of the galvanometer mirror 33V performs a reciprocating motion within a predetermined rotation angle range. This shifts the irradiation position of the light beam from the light source 11 along the V axis. Out of the movements, the movement during the outgoing pass shifts the irradiation position of the light beam, for example, from upside to the down side on the reflection surface of the diagonal mirror 4j, and on the light beam irradiation plane 201, the irradiation position of the light beam shifts, for example, from lower side (this side) to the upper side (back side). The shifting direction of the irradiation position of the light beam may be in an opposite direction.

Further, in the two-dimensional scanning mechanism 33, the data acquired during returning movement within the predetermined rotation angle range of the mirror surface of the galvanometer mirror 33V is not used.

In the two-dimensional scanning mechanism 33, the mirror surface of the galvanometer mirror 33B performs reciprocating motions within a predetermined rotation angle range. This shifts the irradiation position of the light beam from the light source 11 along the B axis. Out of the movements, the movement during the outgoing pass shifts the irradiation position of the light beam, for example, from left side to the right side on the reflection surface of the diagonal mirror 4j, and on the light beam irradiation plane 202. Further, the shifting direction of the irradiation position of the light beam may be in the opposite direction.

When the user diagnoses tooth decay (caries) of a molar using the optical coherence tomographic image generation apparatus 1 having the above-described configuration, it is possible to perform image diagnosis even if the tomographic image 302A (see FIG. 5) is used. However, in a case where the user's attention is directed to adjoining surfaces 203 (see FIG. 7A where tooth of the patient adjoin each other and FIG. 7B, the tomographic image 302L (see FIG. 6) is more preferable for the image diagnosis than the tomographic image 302A (see FIG. 5). In this case, if it is assumed that a tomographic image 203L generated in the first operation mode is displayed on the screen image, there may be a possibility that the hand movement blur may become distinguishable. However, when the tomographic image 302L generated in the second operation mode is displayed on the screen, the image has no blur due to the hand movement, so that the user can find out the desired tomographic plane more quickly from the clear image.

As described above, since the optical coherence tomographic image generation apparatus 1 has the first operation mode and the second operation mode of which scanning directions on the light beam irradiation planes are orthogonal with each other. The first operation mode can generate the tomographic image 302L of which generation period is long, and the second operation mode can generate the tomographic image 302L of which generation period is short. Accordingly, when the tomographic image 302L is displayed on the screen, the blur due to the hand movement can be reduced by selecting the second operation mode.

As described above, the optical coherence tomographic image generation apparatus according to the present invention based on the embodiment. However, the present invention is not limited to this. For example, the embodiment has been described in the case the galvanometer mirror is used as the two-dimensional scanning mechanism 33. However, the present invention is not limited to this, but may be provided using a two-dimensional MEMS (Micro Electro Mechanical Systems) mirror can be used. An element of the two-dimensional MEMS mirror is formed in a three-layer structure of a silicone layer, a ceramic pedestal, and a permanent magnet, the silicone layer is formed including a mirror for total reflection of a light beam and a movable structure such as flat surface coils, etc, for electromagnetic driving by generating an electromagnetic forces are formed. This provides a control for statically or dynamical inclinations in the X-axis direction and the Y-axis direction in proportion to magnitudes of currents flowing through the coils.

Further, in the embodiment, as the light source, the SS-OCT system is used. However, a light source of an SD-OCT (Spectrum Domain Optical Coherence Tomography) or TD-OCT (Time Domain Optical Coherence Tomography) can be also used.

Further, in the present invention, the measuring object is not limited to the molar. In addition, the present invention is also applicable to devices for medical use other than the dental use, and to a nondestructive inspection, etc.

DESCRIPTION OF REFERENCE SYMBOLS 1 optical coherence tomographic image generation apparatus
3 housing
3a scanning mechanism housing part
3b grip
3c nozzle
4, 4B supporting body
4a rod part
4b connecting part
4c coupling tubular member
4d opening
4e connecting part
4h flange part
4i bending part
4j diagonal mirror
10 optical unit
11 light source
12, 16 coupler
13 sampling arm
14, 18 circulator
15, 22 polarization controller
17 reference arm
19 collimator lens
20 condenser lens
21 reference mirror
23 detector
30 probe
31 shutter
32 collimator lens
33 two-dimensional scanning mechanism
33B, 33V galvanometer mirror
34 condenser lens
38 tip member
50 controller
51 A/D converting circuit
52 D/A converting circuit
53 two-dimensional scanning mechanism control circuit
54 display device
100 OCT control device
200 measuring object

The invention claimed is:

1. An optical coherence tomographic image generation apparatus comprising:
a probe including a grip part, a nozzle, and a two-dimensional scanning mechanism therein reflecting a light beam incident from one of sides of the grip part and the nozzle toward another side of the grip part and the nozzle while a position of the light beam is shifted by time-division drive;
an optical unit that divides a light beam emitted from a light source into a measurement light beam and a reference light beam and detects an optical coherent light created by making interference between the reference light beam and scattered light returned by reflection from the measuring object which is irradiated through the probe with the measurement light beam, the optical coherence tomographic image generation apparatus generating a three-dimensional optical coherent tomographic image from the detection signal of the coherent light acquired in a time base; and
a controller having a first operation mode in which main scanning is performed in parallel in a first direction on an optical irradiation plane at the measuring object and a second operation mode in which the main scanning is performed in parallel in a second direction on the optical irradiation plane at the measuring object, the second direction being orthogonal with the first direction,
wherein, when the optical tomographic image of a tomographic plane including a depth direction along the irradiation direction of the measurement light is displayed, time for generating the tomographic image is shortened by switching to either of the first operation mode or the second operation mode selected such that the tomographic plane includes the main scanning direction.

2. The optical coherence tomographic image generation apparatus as claimed in claim 1, wherein the two-dimensional scanning mechanism includes two galvanometer mirrors of which rotational axes are orthogonal with each other.

3. The optical coherence tomographic image generation apparatus as claimed in claim 1, wherein the probe includes a supporting part including a diagonal mirror that changes an optical axis to an orthogonal direction, the supporting part being attached to a tip portion of the nozzle.

4. The optical coherence tomographic image generation apparatus as claimed in claim 2, wherein the probe includes a supporting part including a diagonal mirror that changes an optical axis to an orthogonal direction, the supporting part being attached to a tip portion of the nozzle.

5. The optical coherence tomographic image generation apparatus as claimed in claim 1, wherein the main scanning is performed to successively acquire data of a line at a predetermined number of points more than one in the first direction on the optical irradiation plane in the first mode and in the second direction on the optical irradiation plane in the second mode.

6. The optical coherence tomographic image generation apparatus as claimed in claim 3, wherein the supporting part supports the diagonal mirror at one end thereof, wherein the nozzle includes a connecting part which supports the supporting part at another end of the supporting part detachably.

7. The optical coherence tomographic image generation apparatus as claimed in claim 3, wherein the supporting part is disposed on one side of the optical axis opposite to the orthogonal direction to allow the diagonal mirror to be in contact to the measuring object.

8. The optical coherence tomographic image generation apparatus as claimed in claim 3, wherein the supporting part supports the diagonal mirror at one end thereof, wherein the nozzle includes a connecting part which supports the supporting part at another end of the supporting part detachably.

* * * * *